United States Patent [19]
Leadbetter et al.

[11] Patent Number: 5,688,983
[45] Date of Patent: Nov. 18, 1997

[54] PROCESS FOR THE PREPARATION OF TETRAETHYL METHYLENEBISPHOSPHONATE

[75] Inventors: Michael R. Leadbetter, San Leandro; Richard W. Brown, Moraga; Maureen M. McKenna, Alameda, all of Calif.

[73] Assignee: Zeneca Limited, London, England

[21] Appl. No.: 614,234

[22] Filed: Mar. 12, 1996

[51] Int. Cl.$^6$ .................................................. C07F 9/40
[52] U.S. Cl. .................................................. 558/136
[58] Field of Search .................................................. 558/136

[56] References Cited

PUBLICATIONS

G.M. Kosolapoff, "The Chemistry of Aliphatic Phosphonic Acids, I. Alkylation of Methanediphosphonic Acid," *Journal of the American Chemical Society*, vol. 75, 1500–1501 (1952).

O.E.O. Hormi et al., "A Cheap One–Pot Approach to Tetraethyl Methylenediphosphonate," *Synthetic Communications*, 20(12), 1865–1867 (1990).

Guozheng Liu, "Improved synthesis of tetraethyl methylenediphosphonate" Yingyong Huaxue Oct. 1995 12(5) 103–104.

*Primary Examiner*—C. Warren Ivy
*Assistant Examiner*—Jean F. Vollano
*Attorney, Agent, or Firm*—Joseph R. Snyder

[57] ABSTRACT

This invention relates to a process for the preparation of tetraethyl methylenebisphosphonate by the reaction of dichloromethane with diethyl phosphite, wherein the reaction is performed in a polar aprotic solvent or mixtures thereof.

13 Claims, No Drawings

PROCESS FOR THE PREPARATION OF TETRAETHYL METHYLENEBISPHOSPHONATE

This invention relates to a process for the preparation of tetraethyl methylene-bisphosphonate by the reaction of dichloromethane with diethyl phosphite, wherein the reaction is performed in a polar aprotic solvent or mixtures thereof.

BACKGROUND OF THE INVENTION

The compound, tetraethyl methylenebisphosphonate of formula (I)

$$(CH_3CH_2O)_2-\overset{O}{\underset{\|}{P}}-CH_2-\overset{O}{\underset{\|}{P}}-(OCH_2CH_3)_2 \quad (I)$$

is a useful intermediate for a variety of purposes. For instance, certain aza bisphosphonic acid compounds are described in PCT application publication number WO 95/10188 as having herbicidal activity. An intermediate in the synthetic generation of these bisphosphonic acids is tetraethyl methylenebisphosphonate.

In addition to the above utility, tetraethyl methylenebisphosphonate may be converted to ethylidenebisphosphonate which is useful as a pharmaceutical intermediate and as a monomer for the preparation of phosphorous containing polymers.

An article entitled "The Chemistry of Aliphatic Phosphonic Acids, I. Alkylation of Methanediphosphonic Acid," by G. M. Kosolapoff, in the *Journal of the American Chemical Society*, vol. 75, 1500–1501, (1952), teaches the synthesis of tetraethyl methylenebisphosphonate. This article discloses the process wherein methylene iodide is reacted with triethyl phosphite. After being heated, the reaction mixture is distilled under reduced pressure to produce tetraethyl methylene-bisphosphonate in a yield of 18%.

A more recent article entitled "A Cheap One-pot Approach to Tetraethyl Methylenediphosphonate," by O. E. O. Hormi et al., in *Synthetic Communications*, 20(12), 1865–1867 (1990), teaches the synthesis of tetraethyl methylene-bisphosphonate using dichloromethane, diethyl phosphite, sodium metal and ethanol. In that procedure, diethyl phosphite is added to a sodium ethoxide solution. After about an hour, the solution is concentrated on a rotary evaporator and the residue is dissolved in dichloromethane. After about 2 weeks of stirring, the mixture is washed with water and the dichloromethane layer is dried with magnesium sulfate and again concentrated on a rotary evaporator. The procedure generated a 51% yield of tetraethyl methylenebisphosphonate.

It would be desirable to reduce the reaction time and increase the yield of tetraethyl methylenebisphosphonate over the above procedures. The inventors have found that employing polar aprotic solvents or mixtures thereof, can dramatically increase the reaction rate and the product yield.

Although dichloromethane is still used as a reagent, it has now been surprisingly found that using a polar aprotic solvent in lieu of some or all of dichloromethane as a solvent, speeds the reaction time and improves the yield of tetraethyl methylenebisphosphonate.

SUMMARY OF THE INVENTION

The present invention provides a process for preparing tetraethyl methylene-bisphosphonate having the following formula (I)

$$(CH_3CH_2O)_2-\overset{O}{\underset{\|}{P}}-CH_2-\overset{O}{\underset{\|}{P}}-(OCH_2CH_3)_2 \quad (I)$$

This process includes:
reacting a compound of formula (II)

$$(CH_3CH_2O)_2-\overset{O}{\underset{\|}{P}}-M \quad (II)$$

wherein M is selected from the group consisting of alkali metals, alkaline earth metals and hydrogen, with dichloromethane in the presence of at least one polar aprotic solvent.

DETAILED DESCRIPTION OF THE INVENTION

This invention relates to a process for the preparation of tetraethyl methylene-bisphosphonate by the reaction of dichloromethane with diethyl phosphite. The reaction is performed in the presence of at least one polar aprotic solvent. The inventive process can be represented schematically as follows:

$$2(CH_3CH_2O)_2-\overset{O}{\underset{\|}{P}}-M \xrightarrow[\text{solvent}]{CH_2Cl_2}$$

$$(CH_3CH_2O)_2-\overset{O}{\underset{\|}{P}}-CH_2-\overset{O}{\underset{\|}{P}}-(OCH_2CH_3)_2$$

wherein M is selected from the group consisting of alkali metals, alkaline earth metals and hydrogen. An alkali metal is a metal in Group 1A of the periodic table, such as lithium, sodium and potassium. An alkaline earth metal is a metal in Group IIA of the periodic table, such as calcium, magnesium and barium.

In a reaction vessel, a strong base is suspended in a suitable volume of tetrahydrofuran or another appropriate solvent. Suitable strong bases include sodium hydride, potassium hydride and sodium ethoxide. Other strong bases will be apparent to those skilled in the art. Sodium hydride is preferred.

Next, diethyl phosphite is added to the suspension and the exothermic reaction mixture is stirred to generate the anion of diethyl phosphite. The mole ratio of strong base to diethyl phosphite is greater than or equal to one. Preferably, there is a slight excess of strong base (mole ratio greater than one).

Afterwards, dichloromethane is added in the presence of a polar aprotic solvent. Suitable polar aprotic solvents include, but are not limited to N,N-dimethylformamide, N,N-dimethylacetamide, dimethyl sulfoxide, N-methylpyrrolidinone and acetonitrile or mixtures thereof. N,N-dimethylformamide is preferred. The preferred amount of polar aprotic solvent is 100 mL of polar aprotic solvent per mole of diethyl phosphite. The ratio of dichloromethane to diethyl phosphite is between 1:2 to 2:1. Preferably, a stoichiometric amount of dichloromethane is added compared to diethyl phosphite.

The reaction mixture is heated with stirring until the reaction is complete. The preferred reaction temperature is between 25°–60° C. The product of the reaction, tetraethyl methylenebisphosphonate is isolated in good yield by extractive work-up and vacuum distillation.

The following non-limiting example illustrates the instant invention:

EXAMPLE

To a 5 liter round bottom reaction flask equipped with a thermometer, mechanical stirrer, condenser, nitrogen sweep and addition funnel were added sodium hydride (135 g, 5.3 moles) and 500 mL of tetrahydrofuran. While the reaction mixture was stirred, 700 mL of diethyl phosphite was added dropwise, maintaining the temperature below 60° C. After the addition of the diethyl phosphite was complete, the reaction mixture was cooled to 25° C. and charged sequentially with 500 mL of dimethylformamide and 325 mL of dichloromethane. The reaction mixture was stirred and heated at about 45° C. overnight. The reaction mixture was then cooled and quenched with 1.5 liters of water. The resulting solution was extracted three times with 500 mL of dichloromethane. The organic layers were combined and dried over magnesium sulfate. The dichloromethane was evaporated to produce tetraethyl methylenebisphosphonate in about 90% yield. Although the product was sufficiently pure for further use, it could be purified by vacuum distillation.

Although the invention has been described with reference to preferred embodiments and an example thereof, the scope of the present invention is not limited only to the described embodiments. As will be apparent to persons skilled in the art, modifications and adaptations to the above described invention can be made without departing from the spirit and scope of the invention, which is defined and circumscribed by the appended claims.

What is claimed is:

1. A process for preparing a compound of formula (I)

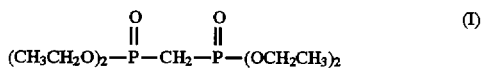

comprising: reacting a compound of the formula (II)

wherein M is selected from the group consisting of alkali metals, alkaline earth metals and hydrogen, with dichloromethane in the presence of at least one polar aprotic solvent other than dichloromethane.

2. A process according to claim 1, wherein the base is selected from the group consisting of sodium hydride, potassium hydride and sodium ethoxide.

3. A process according to claim 1, wherein the polar aprotic solvent is selected from the group consisting of N,N-dimethylformamide, N,N-dimethylacetamide, dimethyl sulfoxide, N-methyl-pyrrolidinone, acetonitrile and mixtures thereof.

4. A process according to claim 1, wherein M is an alkali metal.

5. A process according to claim 4, wherein M is an alkali metal selected from the group consisting of lithium, sodium and potassium.

6. A process according to claim 1, wherein M is an alkaline earth metal.

7. A process according to claim 6, wherein M is an alkaline earth metal selected from the group consisting of calcium, magnesium and barium.

8. A process according to claim 1, wherein the amount of polar aprotic solvent to moles of diethyl phosphite is 100 mL to 1 mole.

9. A process according to claim 3, wherein the polar aprotic solvent is dimethyl sulfoxide.

10. A process according to claim 3, wherein the polar aprotic solvent is N,N-dimethylformamide.

11. A process according to claim 1, wherein the ratio of dichloromethane to a compound of formula II is between 1:2 to 1:1.

12. A process according to claim 1, wherein the ratio of dichloromethane to a compound of formula II is 1:2.

13. A process for preparing a compound of formula (I)

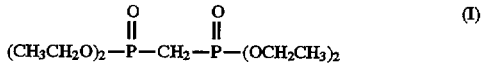

comprising the steps of:

a) reacting diethylphosphite with a base to form a compound of formula (II)

wherein M is selected from the group consisting of an alkali metal, an alkaline earth metal and hydrogen; and b) reacting dichloromethane with said compound of formula II in the presence of a polar aprotic solvent or mixtures thereof other than dichloromethane.

* * * * *